(12) United States Patent
Fujino et al.

(10) Patent No.: US 7,687,066 B2
(45) Date of Patent: *Mar. 30, 2010

(54) SELF EMULSIFYING OILY LIQUID COSMETIC

(75) Inventors: Jin Fujino, Yokohama (JP); Keiichi Oyama, Yokohama (JP); Kazuhito Uchida, Yokkaichi (JP)

(73) Assignee: The Nisshin OilliO Group, Ltd., Tokyo (JP)

( * ) Notice: Subject to any disclaimer, the term of this patent is extended or adjusted under 35 U.S.C. 154(b) by 1109 days.

This patent is subject to a terminal disclaimer.

(21) Appl. No.: 10/556,177

(22) PCT Filed: May 7, 2004

(86) PCT No.: PCT/JP2004/006469

§ 371 (c)(1),
(2), (4) Date: Nov. 7, 2005

(87) PCT Pub. No.: WO2004/098544

PCT Pub. Date: Nov. 18, 2004

(65) Prior Publication Data

US 2006/0286133 A1    Dec. 21, 2006

(30) Foreign Application Priority Data

May 9, 2003  (JP) ............................ 2003-131782
Dec. 2, 2003 (JP) ............................ 2003-403334

(51) Int. Cl.
C08G 63/48 (2006.01)
A61K 8/02 (2006.01)

(52) U.S. Cl. ..................... 424/401; 528/295.5

(58) Field of Classification Search .............. 424/401; 528/295.5
See application file for complete search history.

(56) References Cited

U.S. PATENT DOCUMENTS

| | | | |
|---|---|---|---|
| 4,454,113 A | 6/1984 | Hemker | |
| 5,147,644 A | 9/1992 | Oppenlaender et al. | |
| 5,397,497 A | 3/1995 | Jakobson et al. | |
| 6,506,391 B1 | 1/2003 | Biatry | |
| 2004/0115161 A1 | 6/2004 | Oyama | |
| 2006/0286133 A1 | 12/2006 | Fujino et al. | |

FOREIGN PATENT DOCUMENTS

| | | |
|---|---|---|
| CN | 1278704 A | 1/2001 |
| EP | 1 623 694 A1 | 2/2006 |
| JP | 58-185537 | 10/1983 |
| JP | 62-250941 A | 10/1987 |
| JP | 01-176446 | 7/1989 |
| JP | 02-172938 | 7/1990 |
| JP | 5-310625 A | 11/1993 |
| JP | 6-157289 A | 6/1994 |
| JP | 7-100355 A | 4/1995 |
| JP | 7-173380 A | 7/1995 |
| JP | 07-185294 | 7/1995 |
| JP | 7-187947 | 7/1995 |
| JP | 7-308560 A | 11/1995 |
| JP | 8-143513 A | 6/1996 |
| JP | 09-208444 | 8/1997 |
| JP | 11-152205 | 6/1999 |
| JP | 11-262653 A | 7/1999 |
| JP | 2003-55128 A | 2/2003 |
| JP | A 2004-035420 | 2/2004 |
| JP | 2004-256514 | 9/2004 |
| JP | 3891982 | 3/2007 |
| WO | WO 99/20111 | 4/1999 |
| WO | WO 02/078650 A | 10/2002 |

OTHER PUBLICATIONS

Office Action for Chinese Patent Application No. 200480012310X, dated Jun. 8, 2007.
English translation of the Office Action for Chinese Patent Application No. 200480012310X, dated Jun. 8, 2007.
International Search Report from PCT priority application Serial No. PCT/JP2004/006469.
Written Opinion from PCT priority application Serial No. PCT/JP2004/006469.
Sagitani et al., The Mechanism for Formation of Homogeneous and Fine Droplet O/W Emulsions by Nonionic Surfactants, *Petrochemistry*. 30(1):38-43 (1981).
The European Search Report issued in corresponding European Patent Application No. 04819389, dated Jun. 29, 2009.
Database WPI Week 198934, Thomson Scientific, London, GB; an 1989-244471 XP002533007 (Corresponds to Reference No. 7).
Database WPI Week 200467, Thomson Scientific, London, GB; an 2004-680317 XP002533008 (Corresponds to Reference No. 8).
Office Action issued in counterpart Japanese Patent Application No. 2005-506034, dated Jun. 30, 2009.
Notice of Allowance issued in counterpart Japanese Patent Application No. 2004-186841, dated Sep. 29, 2009.
Streitwieser et al., "Introduction to Organic Chemistry," Third Edition, *Macmillan Publishing Company*, pp. 509-510, 1985.

*Primary Examiner*—Gina C Yu
(74) *Attorney, Agent, or Firm*—Knobbe, Martens, Olson & Bear, LLP

(57) ABSTRACT

A self emulsification type oily liquid cosmetic composition includes 8 to 30% by mass of the following component A and 50 to 92% by mass of the following component B.

Component A: a polyglycerin fatty acid ester having a hydroxyl value of 450 to 700, and a branched fatty acid residue having 16 to 18 carbon atoms and/or a linear unsaturated fatty acid residue having 16 to 18 carbon atoms accounting for 50 to 100% by mass of total constituent fatty acid residues, and in a polyglycerin constituting the polyglycerin fatty acid ester, a total content of a polyglycerin cyclic compound of a dimer and a trimer is from 0 to 3% based on the entire polyglycerin, a total content of a polyglycerin of a undecamer or a higher multimer is from 10 to 30% based on the entire polyglycerin, and each content of a polyglycerin of a tetramer to a decamer is from 4 to 20% based on the entire polyglycerin.

Component B: an oily component.

31 Claims, No Drawings

SELF EMULSIFYING OILY LIQUID COSMETIC

This application is the U.S. National Phase under 35 U.S.C. §371 of International Application PCT/JP2004/006469, filed May 7, 2004, which claims priority to Japanese Patent Application No. 2003-403334, filed Dec. 2, 2003 and Japanese Patent Application No. 2003-131782, filed May 9, 2003. The International Application was published under PCT Article 21(2) in a language other than English.

TECHNICAL FIELD

The present invention relates to a self emulsification type oily liquid cosmetic composition containing a specific polyglycerin fatty acid ester and an oily component as bases.

BACKGROUND ART

When a self emulsification type oily liquid cosmetic composition contacts with water, phase reversal of emulsion occurs to produce an oil-in-water type emulsion, and typical examples of the self emulsification type oily liquid cosmetic composition include a cleansing cosmetic composition, a bath cosmetic composition, and the like.

It has recently been required for a makeup cosmetic to attain a long wear for makeup and also tendency such as heavy makeup increases in accordance with a trend. Therefore, it is required to develop a cleansing cosmetic composition having strong detergency for the purpose of removing makeup cosmetic compositions containing an oily component as a base, such as foundation and lipstick.

The cleansing cosmetic compositions in various preparation forms are on the market and examples thereof include water-based cleansing cosmetic composition, oil-based cleansing cosmetic composition, polyhydric alcohol-based cleansing cosmetic composition, and liquid crystal-based cleansing cosmetic composition containing a surfactant in the preparation forms such as liquid, gel and cream. Among these cleansing cosmetic compositions, it is known that an oily liquid cleansing cosmetic composition is excellent in compatibility with an oily component of a cosmetic and is therefore most excellent in detergency. Consequently, a product (cleansing cosmetic composition), which is most popular on the market, is a self emulsification type oily product including a mixture of an oily component and a surfactant. This product has a property such that phase inversion quickly occurs when contacted with water. At first, stains are migrated (dissolved) in the oily component by applying the cleansing cosmetic composition well to makeup stains. And then, the cleansing cosmetic composition is contacted with water to produce an oil-in-water type emulsion of the oily component containing stains, and thus makeup stains can be removed by washing out with water.

The self emulsification type oily liquid cosmetic composition must contain a high concentration such as 8 to 30% by mass of a surfactant so as to quickly self-emulsify when contacted with water. Examples of a conventional surfactant used in the self emulsification type oily liquid cosmetic composition include polyoxyethylene sorbitan branched fatty acid ester, polyethylene glycol branched fatty acid ester and polyoxyethylene branched alkyl ether. Among these surfactants, it has conventionally been known that a polyoxyethylene-based surfactant has some safety concerns. When a self emulsification type oily liquid cleansing cosmetic composition containing a high concentration of this polyoxyethylene-based surfactant is directly applied on the skin, there may arise problems such as strong creaky feel after cleansing and skin trouble, and thus there is some safety concerns. The polyoxyethylene-based surfactant has a problem such that it gives drastically poor taste and smell in the mouth. Therefore, with regard to the cleansing cosmetic composition which sometimes penetrates into the mouth when used in the face portion, especially when used to remove lipstick, users feel drastic discomfort.

To solve the problem of the cosmetic composition using the polyoxyethylene-based surfactant, for example, Japanese Unexamined Patent Application, First Publication No. Sho 58-185537 discloses a cosmetic composition using a polyglycerin fatty acid ester.

A surfactant which has high safety and is free from discomfort flavor and is also commonly used in foods includes, for example, a polyglycerin fatty acid ester. However, most polyglycerin fatty acid esters on the market are not easily dissolved in an oily component. Even when dissolved in the oily component, there arises a problem that the compositions are not self-emulsified because of poor dispersibility in water. Therefore, a self emulsification type oily cleansing cosmetic composition including the polyglycerin fatty acid ester and the oily component is inferior in storage stability of the product (cleansing cosmetic composition) because of poor solubility (not easily dissolved in the oily component). Alternatively, stains can not be washed out because of poor dispersibility in water, and the oily component is remained on the skin, resulting in strong greasy feel. Therefore, in the self emulsification type oily cleansing cosmetic composition, the polyglycerin fatty acid ester was merely used as an auxiliary emulsifier.

A conventional self emulsification type oily liquid cleansing cosmetic composition had a problem that, in case of cleansing hard-to-remove cosmetic compositions such as heavy-coated foundation and mascara containing oil-resistant and water-resistant components, the skin tends to be rubbed strongly during a process of applying the cleansing cosmetic composition to these hard-to-remove cosmetic compositions to raise makeup stains, and thus causing problems such as skin trouble and eyelash removal. In a next process of self-emulsifying by contacting with water, the cleansing cosmetic composition becomes a liquid crystal and a white gel-like material, and then is dispersed in water. However, the cleansing cosmetic composition is not quickly dispersed in water and is therefore remained on the skin to give long-term slimy feel, and also rinsing requires a long time.

By the way, a bath cosmetic composition is often used during bathing so as to prevent skin irritations, cracks and chaps and to improve skin conditions. Examples of the preparation form of the bath cosmetic composition include bath salt, bath oil and herbal medicine. Among these, with regard to a product of a self emulsification type oily bath oil including a mixture of an oily component and a surfactant, when the bath oil is put into bath water, the bath oil is self-emulsified in bath water and the oily component in the form of fine particles is uniformly dispersed in bath water. Thus there can be expected various improving effects peculiar to the oily component, for example, emollient, moisturizing, anti-inflammatory and warm bathing effects.

However, a conventional self emulsification type oily bath cosmetic composition including a mixture of an oily component and a surfactant is insufficient in dispersibility in bath water and is not self-emulsified, and is therefore floated in the preparation form of a bath cosmetic composition. Consequently, the bath cosmetic composition gives greasy feel to cause problems such as poor skin sensation after bathing and adhesion of the bath cosmetic composition onto a bath wall.

For the same reason as in case of the cleansing cosmetic composition, the polyglycerin fatty acid ester is not substantially used as the surfactant of the self emulsification type oily bath cosmetic composition. Even when used, the polyglycerin fatty acid ester was merely used as an auxiliary emulsifier.

An object of the present invention is to solve the problems described above and to provide a self emulsification type oily liquid cosmetic composition which ensures safety for the human body and is excellent in storage stability, and is also excellent in dispersibility in water due to easy self emulsification and is excellent in tactile sensation.

DISCLOSURE OF THE INVENTION

A self emulsification type oily liquid cosmetic composition according to a first aspect of the present invention includes 8 to 30% by mass of the following component A and 50 to 92% by mass of the following component B.

Component A: a polyglycerin fatty acid ester having a hydroxyl value of 450 to 700, and a branched fatty acid residue having 16 to 18 carbon atoms and/or a linear unsaturated fatty acid residue having 16 to 18 carbon atoms accounting for 50 to 100% by mass of total constituent fatty acid residues, and in a polyglycerin constituting the polyglycerin fatty acid ester, a total content of a polyglycerin cyclic compound of a dimer and a trimer is from 0 to 3% based on the entire polyglycerin, a total content of a polyglycerin of a undecamer or a higher multimer is from 10 to 30% based on the entire polyglycerin, and each content of a polyglycerin of a tetramer to a decamer is from 4 to 20% based on the entire polyglycerin.

Component B: an oily component.

The self emulsification type oily liquid cosmetic composition according to the aspect of the present invention ensures safety and is excellent in dispersibility in water, thereby being easily self-emulsified, and is also excellent in storage stability. When this self emulsification type oily liquid cosmetic composition is used as a cleansing cosmetic composition, the oily component is not remained on a skin. Therefore, pimple and eruption caused by the remained oily component can be prevented. Furthermore, the self emulsification type oily liquid cosmetic composition can be applied to cosmetic compositions (including quasi drugs) such as cosmetic oil, hair cleansing, massage oil and hair treatment and drugs.

In the self emulsification type oily liquid cosmetic composition according to the first aspect of the present invention, the branched fatty acid residue having 16 to 18 carbon atoms may be an isostearic acid residue and the linear unsaturated fatty acid residue having 16 to 18 carbon atoms may be an oleic acid residue. In this case, storage stability at high temperature of the self emulsification type oily liquid cosmetic composition is further improved.

In the self emulsification type oily liquid cosmetic composition according to the first aspect of the present invention, a content of water may be from 0 to 2% by mass. In this case, deterioration of storage stability is suppressed and also no gel is produced and excellent water dispersibility is obtained.

The self emulsification type oily liquid cosmetic composition according to the first aspect of the present invention may contain no water. In this case, excellent storage stability and water dispersibility are obtained.

The self emulsification type oily liquid cosmetic composition according to the first aspect of the present invention may have electric conductivity at 25° C. of 0.1 µS/cm or less and may have properties capable of uniformly dissolving and dispersing in a hydrocarbon solvent. In this case, it is an oily cosmetic composition in which an oil in the self emulsification type oily liquid cosmetic composition is a continuous phase and is excellent in compatibility with the oily component.

In the self emulsification type oily liquid cosmetic composition according to the first aspect of the present invention, a content of a hydrocarbon oil in the oily component as the component B may be less than 10% by mass based on the self emulsification type oily liquid cosmetic composition. In-this case, the self emulsification type oily liquid cosmetic composition is more excellent in dispersibility in water and can be easily self-emulsified.

The self emulsification type oily liquid cosmetic composition according to the first aspect of the present invention may be a cleansing cosmetic composition. In this case, since the cleansing cosmetic composition is excellent in dispersibility in water and can be easily self-emulsified, the oily component is not remained on the skin. Therefore, pimple and eruption caused by the remained oily component can be prevented. Furthermore, since the cleansing cosmetic composition is excellent in compatibility with a cosmetic composition, the cleansing cosmetic composition is excellent in stain removal degree of makeup stains. The cleansing cosmetic composition is free from greasy feel and creaky feel after cleansing and is free from slimy feel upon washing out, and is also easily rinsed, and thus excellent tactile sensation is obtained.

The self emulsification type oily liquid cosmetic composition according to the first aspect of the present invention may be a bath cosmetic composition. In this case, the bath cosmetic composition is quickly self-emulsified when contacted with water and is uniformly dispersed. Therefore, the bath cosmetic composition is excellent in dispersibility in bath water. Furthermore, the bath cosmetic composition gives excellent moist feel and is free from greasy feel, and thus excellent tactile sensation is obtained. Excellent storage stability is also obtained.

A self emulsification type oily liquid cosmetic composition according to a second aspect of the present invention includes 10 to 25% by mass of the following component A and 65 to 85% by mass of the following component B.

Component A: a polyglycerin fatty acid ester having a hydroxyl value of 450 to 700, and a branched fatty acid residue having 16 to 18 carbon atoms and/or a linear unsaturated fatty acid residue having 16 to 18 carbon atoms accounting for 50 to 100% by mass of total constituent fatty acid residues, and in a polyglycerin constituting the polyglycerin fatty acid ester, a total content of a polyglycerin cyclic compound of a dimer and a trimer is from 0 to 3% based on the entire polyglycerin, a total content of a polyglycerin of a undecamer or a higher multimer is from 10 to 30% based on the entire polyglycerin, and each content of a polyglycerin of a tetramer to a decamer is from 4 to 20% based on the entire polyglycerin.

Component B: an oily component.

The self emulsification type oily liquid cosmetic composition according to the second aspect of the present invention ensures safety and is excellent in dispersibility in water, thereby being easily self-emulsified, and is also excellent in storage stability. When this self emulsification type oily liquid cosmetic composition is used as a cleansing cosmetic composition, the oily component is not remained on the skin. Therefore, pimple and eruption caused by the remained oily component can be prevented. Furthermore, the self emulsification type oily liquid cosmetic composition can be applied to cosmetic compositions (including quasi drugs) such as cosmetic oil, hair cleansing, massage oil and hair treatment and drugs.

The self emulsification type oily liquid cosmetic composition according to the second aspect of the present invention may further contain lecithin in a content of 1 to 10% by mass based on a content of the component A. In this case, self emulsification properties of the self emulsification type oily liquid cosmetic composition can be further improved.

In the self emulsification type oily liquid cosmetic composition according to the second aspect of the present invention, a content of water may be from 0 to 2% by mass. In this case, deterioration of storage stability is suppressed and also no gel is produced and excellent water dispersibility is obtained.

The self emulsification type oily liquid cosmetic composition according to the second aspect of the present invention may contain no water. In this case, excellent storage stability and water dispersibility are obtained.

The self emulsification type oily liquid cosmetic composition according to the second aspect of the present invention may have electric conductivity at 25° C. of 0.1 μS/cm or less and may have properties capable of uniformly dissolving and dispersing in a hydrocarbon solvent. In this case, it is an oily cosmetic composition in which an oil in the self emulsification type oily liquid cosmetic composition is a continuous phase and is excellent in compatibility with the oily component.

In the self emulsification type oily liquid cosmetic composition according to the second aspect of the present invention, a content of a hydrocarbon oil in the oily component as the component B may be less than 10% by mass based on the self emulsification type oily liquid cosmetic composition. In this case, the self emulsification type oily liquid cosmetic composition is more excellent in dispersibility in water and can be easily self-emulsified.

The self emulsification type oily liquid cosmetic composition according to the second aspect of the present invention may be a cleansing cosmetic composition. In this case, since the cleansing cosmetic composition is excellent in dispersibility in water and can be easily self-emulsified, the oily component is not remained on the skin. Therefore, pimple and eruption caused by the remained oily component can be prevented. Furthermore, since the cleansing cosmetic composition is excellent in compatibility with a cosmetic composition, the cleansing cosmetic composition is excellent in stain removal degree of makeup stains. The cleansing cosmetic composition is free from greasy feel and creaky feel after cleansing and is free from slimy feel upon washing out, and is also easily rinsed, and thus excellent tactile sensation is obtained.

The self emulsification type oily liquid cosmetic composition according to the second aspect of the present invention may be a bath cosmetic composition. In this case, the bath cosmetic composition is quickly self-emulsified when contacted with water and is uniformly dispersed. Therefore, the bath cosmetic composition is excellent in dispersibility in bath water. Furthermore, the bath cosmetic composition gives excellent moist feel and is free from greasy feel, and thus excellent tactile sensation is obtained. Excellent storage stability is also obtained.

A self emulsification type oily liquid cosmetic composition according to a third aspect of the present invention includes 8 to 30% by mass of the following component A, 65 to 90% by mass of the following component B and 0.1 to 100% by mass of the following component C based on a content of the component A.

Component A: a polyglycerin fatty acid ester having a hydroxyl value of 550 to 700, and a branched fatty acid residue having 16 to 18 carbon atoms and/or a linear unsaturated fatty acid residue having 16 to 18 carbon atoms accounting for 50 to 100% by mass of total constituent fatty acid residues, and in a polyglycerin constituting the polyglycerin fatty acid ester, a total content of a polyglycerin cyclic compound of a dimer and a trimer is from 0 to 3% based on the entire polyglycerin, a total content of a polyglycerin of a undecamer or a higher multimer is from 10 to 30% based on the entire polyglycerin, and each content of a polyglycerin of a tetramer to a decamer is from 4 to 20% based on the entire polyglycerin.

Component B: an oily component.

Component C: a polyhydric alcohol fatty acid ester having a hydroxyl value of 100 to 500 (excluding the component A) and/or a polyhydric alcohol alkyl ether having a hydroxyl value of 100 to 500.

The self emulsification type oily liquid cosmetic composition according to the third aspect of the present invention ensures safety and is excellent in dispersibility in water, thereby being easily self-emulsified, and is also excellent in storage stability. When this self emulsification type oily liquid cosmetic composition is used as a cleansing cosmetic composition, the oily component is not remained on the skin. Therefore, pimple and eruption caused by the remained oily component can be prevented. Furthermore, the self emulsification type oily liquid cosmetic composition can be applied to cosmetic compositions (including quasi drugs) such as cosmetic oil, hair cleansing, massage oil and hair treatment and drugs.

In the self emulsification type oily liquid cosmetic composition according to the third aspect of the present invention, a content of water may be from 0 to 2% by mass. In this case, deterioration of storage stability is suppressed and also no gel is produced and excellent water dispersibility is obtained.

The self emulsification type oily liquid cosmetic composition according to the third aspect of the present invention may contain no water. In this case, excellent storage stability and water dispersibility are obtained.

The self emulsification type oily liquid cosmetic composition according to the third aspect of the present invention may have electric conductivity at 25° C. of 0.1 μS/cm or less and may have properties capable of uniformly dissolving and dispersing in a hydrocarbon solvent. In this case, it is an oily cosmetic composition in which an oil in the self emulsification type oily liquid cosmetic composition is a continuous phase and is excellent in compatibility with the oily component.

In the self emulsification type oily liquid cosmetic composition according to the third aspect of the present invention, a content of a hydrocarbon oil in the oily component as the component B may be less than 10% by mass based on the self emulsification type oily liquid cosmetic composition. In this case, the self emulsification type oily liquid cosmetic composition is more excellent in dispersibility in water and can be easily self-emulsified.

The self emulsification type oily liquid cosmetic composition according to the third aspect of the present invention may be a cleansing cosmetic composition. In this case, since the cleansing cosmetic composition is excellent in dispersibility in water and can be easily self-emulsified, the oily component is not remained on the skin. Therefore, pimple and eruption caused by the remained oily component can be prevented. Furthermore, since the cleansing cosmetic composition is excellent in compatibility with a cosmetic composition, the cleansing cosmetic composition is excellent in stain removal degree of makeup stains. The cleansing cosmetic composition is free from greasy feel and creaky feel after cleansing and is free from slimy feel upon washing out, and is also easily rinsed, and thus excellent tactile sensation is obtained.

The self emulsification type oily liquid cosmetic composition according to the third aspect of the present invention may be a bath cosmetic composition. In this case, since the bath cosmetic composition is quickly self-emulsified when contacted with water and is uniformly dispersed, the bath cosmetic composition is excellent in dispersibility in bath water. Furthermore, the bath cosmetic composition gives excellent moist feel and is free from greasy feel, and thus excellent tactile sensation is obtained. Excellent storage stability is also obtained.

A self emulsification type oily liquid cosmetic composition according to a fourth aspect of the present invention includes 10 to 25% by mass of the following component A, 65 to 85% by mass of the following component B and 0.1 to 100% by mass of the following component C based on a content of the component A.

Component A: a polyglycerin fatty acid ester having a hydroxyl value of 550 to 700, and a branched fatty acid residue having 16 to 18 carbon atoms and/or a linear unsaturated fatty acid residue having 16 to 18 carbon atoms accounting for 50 to 100% by mass of total constituent fatty acid residues, and in a polyglycerin constituting the polyglycerin fatty acid ester, a total content of a polyglycerin cyclic compound of a dimer and a trimer is from 0 to 3% based on the entire polyglycerin, a total content of a polyglycerin of a undecamer or a higher multimer is from 10 to 30% based on the entire polyglycerin, and each content of a polyglycerin of a tetramer to a decamer is from 4 to 20% based on the entire polyglycerin.

Component B: an oily component.

Component C: a polyhydric alcohol fatty acid ester having a hydroxyl value of 100 to 500 (excluding the component A) and/or a polyhydric alcohol alkyl ether having a hydroxyl value of 100 to 500.

The self emulsification type oily liquid cosmetic composition according to the fourth aspect of the present invention ensures safety and is excellent in dispersibility in water, thereby being easily self-emulsified, and is also excellent in storage stability. When this self emulsification type oily liquid cosmetic composition is used as a cleansing cosmetic composition, the oily component is not remained on the skin. Therefore, pimple and eruption caused by the remained oily component can be prevented. Furthermore, the self emulsification type oily liquid cosmetic composition can be applied to cosmetic compositions (including quasi drugs) such as cosmetic oil, hair cleansing, massage oil and hair treatment and drugs.

The self emulsification type oily liquid cosmetic composition according to the fourth aspect of the present invention may further contain lecithin in a content of 1 to 10% by mass based on a content of the component A. In this case, self emulsification properties of the self emulsification type oily liquid cosmetic composition can be further improved.

In the self emulsification type oily liquid cosmetic composition according to the fourth aspect of the present invention, a content of water may be from 0 to 2% by mass. In this case, deterioration of storage stability is suppressed and also no gel is produced and excellent water dispersibility is obtained.

The self emulsification type oily liquid cosmetic composition according to the fourth aspect of the present invention may contain no water. In this case, excellent storage stability and water dispersibility are obtained.

The self emulsification type oily liquid cosmetic composition according to the fourth aspect of the present invention may have electric conductivity at 25° C. of 0.1 µS/cm or less and may have properties capable of uniformly dissolving and dispersing in a hydrocarbon solvent. In this case, it is an oily cosmetic composition in which an oil in the self emulsification type oily liquid cosmetic composition is a continuous phase and is excellent in compatibility with the oily component.

In the self emulsification type oily liquid cosmetic composition according to the fourth aspect of the present invention, a content of a hydrocarbon oil in the oily component as the component B may be less than 10% by mass based on the self emulsification type oily liquid cosmetic composition. In this case, the self emulsification type oily liquid cosmetic composition is more excellent in dispersibility in water and can be easily self-emulsified.

The self emulsification type oily liquid cosmetic composition according to the fourth aspect of the present invention may be a cleansing cosmetic composition. In this case, since the cleansing cosmetic composition is excellent in dispersibility in water and can be easily self-emulsified, the oily component is not remained on the skin. Therefore, pimple and eruption caused by the remained oily component can be prevented. Furthermore, since the cleansing cosmetic composition is excellent in compatibility with a cosmetic composition, the cleansing cosmetic composition is excellent in stain removal degree of makeup stains. The cleansing cosmetic composition is free from greasy feel and creaky feel after cleansing and is free from slimy feel upon washing out, and is also easily rinsed, and thus excellent tactile sensation is obtained.

The self emulsification type oily liquid cosmetic composition according to the fourth aspect of the present invention may be a bath cosmetic composition. In this case, the bath cosmetic composition is quickly self-emulsified when contacted with water and is uniformly dispersed. Therefore the bath cosmetic composition is excellent in dispersibility in bath water. Furthermore, the bath cosmetic composition gives excellent moist feel and is free from greasy feel, and thus excellent tactile sensation is obtained. Excellent storage stability is also obtained.

BEST MODE FOR CARRYING OUT THE INVENTION

Preferred embodiments of the present invention will now be described with reference to the accompanying drawings. The present invention is not limited to the following embodiments and constituent elements of these embodiments may be appropriately combined.

At first, the self emulsification type oily liquid cosmetic composition according to one aspect (first aspect or second aspect) of the present invention will now be described.

The component A used in the present invention is a polyglycerin fatty acid ester and the hydroxyl value is from 450 to 700, preferably 500 to 650, and more preferably from 550 to 650. Consequently, a self emulsification type oily liquid cosmetic composition having excellent self emulsification properties can be obtained.

When the hydroxyl value is less than 450, self emulsification type oily liquid cosmetic composition is inferior in dispersibility in water because of poor self emulsification properties. When the hydroxyl value is more than 700, the polyglycerin fatty acid ester is inferior in solubility in the oily component. As described above, when the hydroxyl value is less than 450 or more than 700, the purpose of the self emulsification type oily liquid cosmetic composition can not be attained.

The hydroxyl value can be obtained by determining number of milligrams of potassium hydroxide for neutralizing acetic acid required to acetylate free hydroxyl groups contained in 1 g of a sample in accordance with Standard Methods for the Analysis of Fats, Oils and Related Materials.

A branched fatty acid residue having 16 to 18 carbon atoms and/or a linear unsaturated fatty acid residue having 16 to 18 carbon atoms account for 50 to 100% by mass, preferably 55 to 100% by mass, and most preferably 60 to 100% by mass, of total constituent fatty acid residues of the polyglycerin fatty acid ester as the component A. The branched fatty acid residue having 16 to 18 carbon atoms may be either a branched saturated fatty acid or a branched unsaturated fatty acid, however is preferably the branched saturated fatty acid. Consequently, oxidation stability of the polyglycerin fatty acid ester can be more enhanced.

Polyglycerin fatty acid ester which includes linear saturated fatty acid residue having 16 to 18 carbon atoms in a content of 50 to 100% by mass of total constituent fatty acid residues is not preferable because it is not liquid at normal temperature or low temperature.

In the case in which a fatty acid residue having 15 or less carbon atoms is included in a content of 50 to 100% by mass of total constituent fatty acid residues, it is not preferable because self emulsification properties of the self emulsification type oily liquid cosmetic composition deteriorate. In the case in which a fatty acid residue having 19 or more carbon atoms is included in a content of 50 to 100% by mass of total constituent fatty acid residues, it is not preferable because the polyglycerin fatty acid ester becomes insoluble in the oily component.

Examples of the branched fatty acid residue having 16 to 18 carbon atoms include isostearic acid residue (16-methylheptadecanoyl group, 15-methylheptadecanoyl group, 10-methylheptadecanoyl group, multibranched isostearic acid residue) and isopalmitic acid residue (14-methylpentadecanoyl group). In particular, the isostearic acid residue is preferable and the 16-methylheptadecanoyl group is more preferable.

Examples of the linear unsaturated fatty acid residue having 16 to 18 carbon atoms include unsaturated monohydroxy acid residue such as oleic acid residue, palmitoleic acid residue and ricinoleic acid residue. In particular, the oleic acid residue is preferable. A mixed fatty acid residue derived from palm oil containing 50% by mass or more of the oleic acid residue is also included therein.

In the polyglycerin constituting the polyglycerin fatty acid ester as the component A, a total content of a polyglycerin cyclic compound of a dimer or a trimer must be within a range from 0 to 3%, more preferably from 0 to 2%, and most preferably from 0 to 1%. The reason is as follows. When the total content of the polyglycerin cyclic compound of the dimer or trimer is more than 3%, the self emulsification type oily liquid cosmetic composition is inferior in self emulsification properties and dispersibility in water becomes inferior, thereby separation is caused during storage.

In the polyglycerin constituting the polyglycerin fatty acid ester as the component A, a total content of the polyglycerin of an undecamer or a higher multimer must be within a range from 10 to 30%, more preferably from 12 to 28%, and most preferably from 15 to 26%. The reason is as follows. When the total content of the polyglycerin of the undecamer or higher multimer is not within a range from 10 to 30% (less than 10% or, more than 30%), the self emulsification type oily liquid cosmetic composition is inferior in self emulsification properties and dispersibility in water becomes inferior.

In the polyglycerin constituting the polyglycerin fatty acid ester as the component A, each content of a polyglycerin of a tetramer to a decamer must be within a range from 4 to 20%, more preferably from 4 to 15%, and most preferably from 5 to 12%. The reason is as follows. When each content of the polyglycerin of the tetramer to the decamer is not within a range from 4 to 20% (less than 4% or more than 20%), the self emulsification type oily liquid cosmetic composition is inferior in self emulsification properties and dispersibility in water becomes inferior, thereby separation is caused during storage.

Here, as the polyglycerin constituting the polyglycerin fatty acid ester as the component A, a monomer (glycerin) may be included. A content of polyglycerin noncyclic compounds of a dimer and a trimer is not specifically limited.

The content of the polyglycerin is preferably measured by a method including converting the polyglycerin into a polyglycerin derivative and separating and quantitatively analyzing the resulting polyglycerin derivative using a GC method (gas chromatography). As the analytical method due to this GC method includes, a method is exemplified which includes using a fused silica capillary tube in which a low polar liquid phase such as methylsilicone is chemically bonded, and analyzing with heating within a temperature range from 100 to 250° C. at a heating rate of 10° C./min. The component can be easily analyzed by this method. Another method described below can also be exemplified. At first, a gas chromatograph is introduced into a double focusing mass spectrograph and, after ionizing by a method such as chemical ionization, and the measurement is conducted. Then, molecular weight at a peak on a gas chromatogram is determined from a molecular weight of a parent ion, and also, a polymerization degree of glycerin is determined by a chemical formula. The component can be simply analyzed by this method. However, methods are not specifically limited to these.

A content of the component A in the self emulsification type oily liquid cosmetic composition of the present invention is from 8 to 30% by mass, preferably from 10 to 25% by mass, and most preferably from 12 to 20% by mass. The reason is as follows. When the content of the component A is less than 8% by mass, self emulsification properties deteriorate. On the other hand, when the content is more than 30% by mass, dispersibility in water becomes inferior.

The content of the polyglycerin constituting the polyglycerin fatty acid ester as the component A may be within the above range. For example, those prepared by dehydration condensation or those prepared from a known starting material such as epichlorohydrin or glycidol by a synthesis and purification method can be applied, and commercially available products can be used. Examples of the commercially available product include Great Oil D-10, Great Oil D-11 and Great Oil D-12 manufactured by Taiyo Kagaku Co., Ltd.

The oily component as the component B used in the present invention usually contains, as a main component, a liquid or pasty oily component which can be used in cosmetics. Examples of the component B include natural animal and vegetable fats and oils, semisynthetic fats and oils, hydrocarbon oil, higher fatty acids, ester oils, glyceride oils, silicone oils, animal or vegetable or synthetic essential oil components, and fat-soluble vitamins. These oily components can be used alone or in combination.

Specific examples of the natural animal and vegetable fats and oils and the semisynthetic fats and oils include avocado oil, linseed oil, almond oil, olive oil, wheat germ oil, sesame oil, rice germ oil, rice bran oil, safflower oil, soybean oil, evening primrose oil, corn oil, rapeseed oil, horse fat, palm oil, palm kernel oil, castor oil, sunflower oil, jojoba oil, macadamia nuts oil, coconut oil, hardened coconut oil, peanut oil and lanolin. These fats and oils can be used alone or in combination.

Examples of the hydrocarbon oil include squalane, squalene, liquid paraffin and petrolatum. Examples of the ester oil include diisobutyl adipate, 2-hexyldecyl adipate, di-2-heptylundecyl adipate, isostearyl isostearate, trimethylolpropane triisostearate, cetyl 2-ethylhexanoate, neopentyl glycol di-2-ethylhexanoate, trimethylolpropane tri-2-ethylhexanoate, pentaerythritol tetra-2-ethylhexanoate, cetyl octanoate, oleyl oleate, octyldodecyl oleate, decyl oleate, neopentyl glycol dicaprate, 2-ethylhexyl succinate, isocetyl stearate, butyl stearate, diisopropyl sebacate, cetyl lactate, tetradecyl lactate, 2-ethylhexyl palmitate, 2-hexyldecyl palmitate, 2-heptylundecyl palmitate, cholesteryl 12-hydroxystearate, phytosteryl oleate, diisosteary malate, paramethoxycinnamic acid ester and pentaerythritol tetrarosinate.

Examples of the glyceride oil include glyceryl triisostearate, glyceryl triisopalmitate, glyceryl tri-2-ethylhexanoate, glyceryl tritetradecanoate and glyceryl diparamethoxycinnamate.monoisooctylate.

Examples of the silicone oil include higher alkoxy-modified silicones, alkyl-modified silicones and higher fatty acid esters-modified silicones, such as dimethylpolysiloxane, methylphenylpolysiloxane, methylhydrogenpolysiloxane, octamethylcyclopentasiloxane, decamethylcyclohexasiloxane and stearoxy silicone. Examples of the fat-soluble vitamin include tocopherol and derivatives thereof, and retinol and derivatives thereof.

The oily component as the component B used in the present invention is not specifically limited to the above-described specific examples. The self emulsification type oily liquid cosmetic composition can also contain a solid oily component as far as it can be maintained in the form of liquid. In the case in which the self emulsification type oily liquid cosmetic composition has a property to be opaque in appearance at 0° C. or lower, which does not cause problems on storage stability such as decomposition and precipitation, a content of a hydrocarbon oil such as liquid paraffin, squalane or petrolatum in the self emulsification type oily liquid cosmetic composition may be controlled to less than 10% by mass.

A content of the oily component as the component B in the self emulsification type oily liquid cosmetic composition of the present invention is from 50 to 92% by mass, preferably from 65 to 85% by mass, and more preferably from 75 to 85% by mass. The reason is as follows. When the content of the oily component as the component B is less than 50% by mass, dispersibility in water deteriorates. On the other hand, when the content is more than 92% by mass, self emulsification properties tend to become inferior.

In the present invention, water is not an essential component. When disadvantages arise in view of control of viscosity and usability of the product, the self emulsification type oily liquid cosmetic composition may contain water as far as the object of the present invention is not adversely affected. A content of water is controlled within a range from 0 to 2% by mass, more preferably from 0 to 1% by mass, and most preferably 0% by mass, that is, the cosmetic composition contains no water.

When the content of water is 2% by mass or more, storage stability of the product (self emulsification type oily liquid cosmetic composition) may deteriorate, and a gel may be produced, thereby water dispersibility may become inferior. Water as used herein includes water extracts of animals and plants, in addition to purified water to be used in the cosmetic.

The self emulsification type oily liquid cosmetic composition as used herein refers to a self emulsification type oily liquid cosmetic composition in which a surfactant is molecular-dissolved or micelle-dissolved in the oily component or a surfactant is dissolved in the oily component in the state of a liquid crystal. A nonaqueous liquid composition, a gel-like composition or a thickened composition, which is obtained by adding an oil phase to a mixture of an aqueous component such as aqueous polyhydric alcohol and a surfactant, described in Japanese Unexamined Patent Application, First Publication No. H09-208444 and Japanese Unexamined Patent Application, First Publication No. H11-152205 is different from that of the present invention because it contains a polyhydric alcohol continuous phase as a base.

In order to confirm what kind of a composition among an oily or aqueous polyhydric alcohol-based composition and a nonaqueous polyhydric alcohol-based composition, the self emulsification type oily liquid cosmetic composition belongs to, there can be used a method for measuring electric conductivity so as to examine whether or not the composition has electrical conduction properties and a method for examining solubility in a hydrocarbon-based solvent (for example, hexane, xylene and the like) in which a polyhydric alcohol-based composition is not easily dissolved.

The self emulsification type oily liquid cosmetic composition of the present invention preferably contains lecithin, thereby self emulsification properties of the self emulsification type oily liquid cosmetic composition can be further improved. Examples of the lecithin include soybean lecithin, egg yolk lecithin and hydrogen-containing lecithin of which saturation is enhanced by adding hydrogen, which are commercially available as conventional products or reagents; however the lecithin are not limited thereto. A content of the lecithin is preferably from 1 to 10% by mass, more preferably from 1 to 8% by mass, and most preferably from 1 to 5% by mass, based on the content of the component A.

In the present invention, it is not essential to contain polyhydric alcohols such as glycerin and 1,3-butylene glycol (1,3-BG). In order to maintain storage stability, an oily component can be added to a polyhydric alcohol continuous phase containing water so as to give a gel-like emulsification type or liquid crystal type cosmetic composition. However, the resulting cleansing cosmetic composition has weak detergency and poor dispersibility in water, thus departing from the object of the present invention (the object can not be attained). Therefore, it is preferable to contain no polyhydric alcohol in the present invention.

Here, the above description is not applied to the unreacted polyglycerin and glycerin remained in the polyglycerin fatty acid ester, or polyhydric alcohols such as 1,3-BG, glycerin and propylene glycol contained in water-soluble extracts.

Examples of a method for confirming that water is not a continuous phase include a method for measuring electric conductivity. Examples of a method for confirming that a polyhydric alcohol is not a continuous phase include a method for dissolving in a hydrocarbon-based solvent such as hexane or xylene. The fact that the resulting product is a self emulsification type oily liquid cosmetic composition of the present invention can be confirmed as follows. That is, electric conductivity at 25° C. measured by a commercially available simple conductivity meter is substantially 0, more specifically, electric conductivity is 0.1 μS/cm or less, and the resulting product is uniformly dissolved and dispersed in the hydrocarbon solvent.

The self emulsification type oily liquid cosmetic composition of the present invention may contain components known in the fields in which the self emulsification type oily liquid cosmetic composition is used, as far as characteristics of the present invention are not adversely affected. Examples thereof include humectants, antioxidants, blood circulation promoters, pH adjustors, sequestering agents, ultraviolet absorbers, extracts, coloring materials and perfumes.

The self emulsification type cosmetic composition of the present invention is prepared by mixing and dissolving the respective components including the component A and the component B while heating at a temperature ranging from 40 to 90° C. If the component A and the component B are dissolved at normal temperature, they may be mixed and dissolved at normal temperature. The self emulsification type cosmetic composition containing a component C or lecithin can be prepared by mixing the component A and the component B with the component C or lecithin while heating at a temperature ranging from 40 to 90° C. In case of mixing with components other than the component A and the component B used essentially in the present invention, the procedure for mixing and dissolving is not specifically limited.

For example, the component A and the component B which are used in the present invention may be simultaneously mixed with a component C or lecithin, or the component B used essentially in the present invention may be mixed and dissolved after mixing and dissolving the component A used essentially in the present invention and the component C or lecithin. The procedure is the same in case of mixing with other components. Stirring is conducted by a known method and an apparatus such as a blade type stirrer, a dispersing machine or a homomixer is not specifically limited.

Specific examples of the self emulsification type oily liquid cosmetic composition of the present invention include a cleansing cosmetic composition and a bath cosmetic composition.

The cleansing cosmetic composition of the present invention ensures safety and is excellent in storage stability, and is also excellent in stain removal degree. Furthermore, the cleansing cosmetic composition is free from greasy feel and creaky feel after cleansing as well as slimy feel upon washing out, and is also easily rinsed.

The bath cosmetic composition of the present invention ensures safety and is excellent in dispersibility in bath water and storage stability, and is also excellent in moist feel.

The self emulsification type oily liquid cosmetic composition according to another aspect (third aspect or fourth aspect) of the present invention will now be described.

The self emulsification type oily liquid cosmetic composition according to another aspect of the present invention and the self emulsification type oily liquid cosmetic composition according to the above-described one aspect (first aspect or second aspect) of the present invention are different in that the former contains a polyglycerin fatty acid ester having a hydroxyl value of 550 to 700 as a component A, 65 to 90% by mass of the component B, and a component C described hereinafter.

Since other compositions are the same as those in the self emulsification type oily liquid cosmetic composition according to the one aspect of the present invention, the description is omitted.

A content of the oily component as the component B in the self emulsification type oily liquid cosmetic composition according to another aspect of the present invention is from 65 to 90% by mass, preferably from 65 to 85% by mass, and more preferably from 65 to 80% by mass.

The component C in the self emulsification type oily liquid cosmetic composition according to another aspect of the present invention is a polyhydric alcohol fatty acid ester having a hydroxyl value of 100 to 500 (excluding the component A) and/or a polyhydric alcohol alkyl ether having a hydroxyl value of 100 to 500.

In particular, the component C is preferably a polyhydric alcohol fatty acid ester having a hydroxyl value of 200 to 450 (excluding the component A) and/or a polyhydric alcohol alkyl ether having a hydroxyl value of 200 to 450.

A content of the component C is from 0.1 to 100% by mass, preferably from 1 to 70% by mass, and more preferably from 5 to 70% by mass, based on the content of the component A.

As the above component C, that is, the polyhydric alcohol fatty acid ester having a hydroxyl value of 100 to 500 (excluding the component A) and/or the polyhydric alcohol alkyl ether having a hydroxyl value of 100 to 500, commercially available products can be used. Examples thereof include glycerin fatty acid ester, sorbitan fatty acid ester, diglycerin fatty acid ester (excluding the component A), polyglycerin fatty acid ester having an average polymerization degree of 3 to 10 (excluding the component A), sucrose fatty acid ester, alkyl glucoside and alkyl glyceryl ether. It is preferable to use glycerin fatty acid ester, diglycerin fatty acid ester (excluding the component A) and polyglycerin fatty acid ester having an average polymerization degree of 3 to 10 (excluding the component A) in combination. The component is preferably in a form of paste or liquid at normal temperature in view of solubility. Here, polyhydric alcohol fatty acid ester having a polyoxyethylene group and polyhydric alcohol alkyl ether having a polyoxyethylene group are not contained.

The present invention will now be described in detail by way of examples, but the present invention is not limited thereto.

Table 1 shows results of component analysis of polyglycerin which is used for preparing polyglycerin fatty acid ester (component A) used in examples and comparative examples.

In the examples, three kinds of polyglycerins, that is, Great Oil D-10, Great Oil D-11 and Great Oil D-12 which were manufactured by Taiyo Kagaku Co., Ltd. were used as the polyglycerin. In the comparative examples, four kinds of polyglycerins, that is, Great Oil S-10, Great Oil S-11, Great Oil S-12 and Great Oil S-13 which were manufactured by Taiyo Kagaku Co., Ltd. were used.

Component analysis was conducted by gas chromatography and component analytical values were calculated by an area percentage method. In the case in which the polyglycerin contains a cyclic compound of a dimer or a trimer, component analytical values of the dimer and trimer in the polyglycerin are respectively expressed as values in which a noncyclic compound and a cyclic compound are combined.

TABLE 1

| Polymerization degree | Monomer | Dimer | Trimer | Tetramer | Pentamer | Hexamer | Heptamer | Octamer | Nonamer | Decamer | Undecamer or higher multimer | To make | Dimer polyglycerin cyclic compound % | Trimer polyglycerin cyclic compound % |
|---|---|---|---|---|---|---|---|---|---|---|---|---|---|---|
| Analysis Example 1 | 6.6 | 6.9 | 7.6 | 8.8 | 9.3 | 9.1 | 8.4 | 7.7 | 7.0 | 6.5 | 22.1 | 100.0 | 0.1 | 0.0 |
| Analysis Example 2 | 0 | 0.7 | 12.5 | 14.1 | 13.6 | 12.3 | 10.5 | 9.4 | 7.0 | 7.5 | 12.4 | 100.0 | 0 | 0.3 |
| Analysis Example 3 | 6.0 | 8.9 | 9.5 | 9.5 | 9.6 | 9.0 | 8.1 | 7.3 | 6.5 | 6.0 | 19.6 | 100.0 | 1.3 | 1.3 |
| Analysis Comparative Example 1 | 2.7 | 19.6 | 18.8 | 13.3 | 10.9 | 8.4 | 6.5 | 5.2 | 4.1 | 3.6 | 6.9 | 100.0 | 7.8 | 7.9 |
| Analysis Comparative Example 2 | 0 | 5.7 | 24.2 | 21.5 | 14.9 | 9.9 | 6.9 | 4.8 | 3.5 | 2.8 | 5.8 | 100.0 | 0 | 0.9 |
| Analysis Comparative Example 3 | 5.3 | 11.1 | 11.3 | 10.3 | 9.8 | 8.9 | 7.8 | 6.9 | 6.0 | 5.5 | 17.1 | 100.0 | 2.6 | 2.6 |
| Analysis Comparative Example 4 | 0 | 2.1 | 3.7 | 1.8 | 48.3 | 14.8 | 2.2 | 10.8 | 4.5 | 1.5 | 10.3 | 100.0 | 0 | 1.4 |

Note)
The above values were calculated by an area percentage method.
(Analysis Examples and Analysis Comparative Examples) Product Name of Various Polyglycerins and Analysis Examples
Great Oil D-10 (Analysis Example 1)
Great Oil D-11 (Analysis Example 2)
Great Oil D-12 (Analysis Example 3)
Great Oil S-10 (Analysis Comparative Example 1)
Great Oil S-11 (Analysis Comparative Example 2)
Great Oil S-12 (Analysis Comparative Example 3)
Great Oil S-13 (Analysis Comparative Example 4)

Using seven kinds of polyglycerins shown in Analysis Examples of Table 1, polyglycerin fatty acid esters were synthesized. Polyglycerin fatty acid esters used in Examples are shown in Table 2 and polyglycerin fatty acid esters used in Comparative Examples are shown in Table 3.

TABLE 2

Polyglycerin fatty acid esters used in Examples

| Name of raw materials | Hydroxyl value | Raw polyglycerin used | Content of branched or linear unsaturated fatty acid residue having 16 to 18 carbon atoms in total constituent fatty acid residues (% by mass) |
|---|---|---|---|
| Polyglycerin oleic acid ester | 608 | Great Oil D-10 (Analysis Example 1) | 90 |
| Polyglycerin oleic acid ester | 586 | Great Oil D-11 (Analysis Example 2) | 84 |
| Polyglycerin oleic acid ester | 592 | Great Oil D-12 (Analysis Example 3) | 90 |
| Polyglycerin oleic acid ester | 485 | Great Oil D-10 (Analysis Example 1) | 90 |
| Polyglycerin isopalmitic acid ester | 622 | Great Oil D-10 (Analysis Example 1) | 90 |
| Polyglycerin isostearic acid ester | 631 | Great Oil D-10 (Analysis Example 1) | 90 |
| Polyglycerin isostearic acid ester | 476 | Great Oil D-10 (Analysis Example 1) | 89 |

TABLE 3

Polyglycerin fatty acid esters used in Comparative Examples

| Name of raw materials | Hydroxyl value | Raw polyglycerin used | Content of branched or linear unsaturated fatty acid residue having 16 to 18 carbon atoms in total constituent fatty acid residues (% by mass) |
|---|---|---|---|
| Polyglycerin oleic acid ester | 610 | Great Oil S-10 (Analysis Comparative Example 1) | 90 |
| Polyglycerin oleic acid ester | 598 | Great Oil S-11 (Analysis Comparative Example 2) | 90 |
| Polyglycerin oleic acid ester | 633 | Great Oil S-12 (Analysis Comparative Example 3) | 90 |
| Polyglycerin oleic acid ester | 482 | Great Oil S-10 (Analysis Comparative Example 1) | 89 |
| Polyglycerin isopalmitic acid ester | 628 | Great Oil D-13 (Analysis Example 4) | 90 |
| Polyglycerin isostearic acid ester | 423 | Great Oil D-10 (Analysis Example 1) | 84 |
| Polyglycerin myristic acid ester | 619 | Great Oil D-11 (Analysis Example 2) | 45 |
| Polyglycerin oleic acid ester | 485 | Great Oil D-10 (Analysis Example 1) | 95 |
| Polyglycerin isopalmitic acid ester | 720 | Great Oil D-10 (Analysis Example 1) | 90 |

(Production Examples of Polyglycerin Fatty Acid Ester)

Using seven kinds of polyglycerin shown in Table 1 as raw materials, various polyglycerin fatty acid esters having different hydroxyl values were synthesized. The results of the preparation of polyglycerin fatty acid esters using Great Oil D-10 (raw polyglycerin of Analysis Example 1) as a raw material are shown below.

In a four-necked flask equipped with a stirrer, a thermometer, a gas blow tube and a water separator, 220 g of polyglycerin, 80 g of oleic acid and 0.1 g of tripotassium phosphate were charged and then esterified by heating at a temperature of 200 to 250° C. in a nitrogen gas flow. After the completion of the reaction, 0.3 ml of phosphoric acid was added to obtain a polyglycerin oleic acid ester having a hydroxyl value of 608 to be used in Example 1.

Polyglycerin fatty acid esters used in the following Examples and Comparative Examples were obtained by charging various fatty acids and polyglycerins so that a predetermined hydroxyl value was attained and then conducting an esterification reaction in a similar way as the process in the above reaction example.

EXAMPLES AND COMPARATIVE EXAMPLES OF CLEANSING COSMETIC COMPOSITIONS

Examples 1 to 13 and Comparative Examples 1 to 15

Polyglycerin fatty acid esters used in Examples and Comparative Examples were synthesized in a similar way as described above using polyglycerin having the formulation shown in Table 1. Cleansing cosmetic compositions were prepared by adding the respective components shown in Table 4 to Table 7, dissolving while heating at a temperature 70 to 80° C. under sufficient stirring, and cooling to room temperature while stirring.

The cleansing cosmetic compositions thus obtained were evaluated with respect to the following items (1), (2) and (3). The results are shown in Table 4 to Table 7. Here, in Table 4 to Table 7, Analysis Examples 1, 2 and 3 as well as Analysis Comparative Examples 1, 2, 3 and 4 show that polyglycerins as raw materials are those analyzed in Analysis Examples 1, 2 and 3 as well as Analysis Comparative Examples 1, 2, 3 and 4.

TABLE 4

(% by mass)

| | Examples | | | | | | |
|---|---|---|---|---|---|---|---|
| | 1 | 2 | 3 | 4 | 5 | 6 | 7 |
| Polyglycerin oleic acid ester Analysis Example 1, Hydroxyl value: 608 | 16.0 | | | | | | |
| Polyglycerin oleic acid ester Analysis Example 2, Hydroxyl value: 586 | | 16.0 | | | | | 30.0 |
| Polyglycerin oleic acid ester Analysis Example 3, Hydroxyl value: 592 | | | 16.0 | | | | |
| Polyglycerin oleic acid ester Analysis Example 1, Hydroxyl value: 485 | | | | 20.0 | | 10.0 | |
| Polyglycerin isopalmitic acid ester Analysis Example 1, Hydroxyl value: 622 | | | | | 15.0 | | |
| Polyglycerin isostearic acid ester Analysis Example 1, Hydroxyl value: 631 | | | | | | | |
| Polyglycerin isostearic acid ester Analysis Example 1, Hydroxyl value: 476 | | | | | | | |
| Diglycerin isostearic acid ester Hydroxyl value: 410 | 4.0 | 4.0 | 4.0 | | 5.0 | | |
| Glycerin oleic acid ester Hydroxyl value: 295 | | | | | | | 10.0 |
| Isooctyl palmitate | 80.0 | 80.0 | 80.0 | 60.0 | 60.0 | 60.0 | 40.0 |

TABLE 4-continued (% by mass)

| | Examples | | | | | | |
|---|---|---|---|---|---|---|---|
| | 1 | 2 | 3 | 4 | 5 | 6 | 7 |
| Glyceryl tri-2-ethylhexanoate | | | | 20.0 | 20.0 | 30.0 | 20.0 |
| To make | 100 | 100 | 100 | 100 | 100 | 100 | 100 |
| Dispersibility in water | ⊚ | ⊚ | ⊚ | ○ | ⊚ | ○ | ○ |
| Slimy feel | ⊚ | ⊚ | ⊚ | ○ | ⊚ | ○ | ○ |
| Rinsing feel | ⊚ | ⊚ | ⊚ | ○ | ⊚ | ○ | ○ |
| Stain removal degree | ⊚ | ⊚ | ⊚ | ⊚ | ⊚ | ○ | ⊚ |
| Greasy feel after cleansing | ⊚ | ⊚ | ⊚ | ○ | ⊚ | ○ | ⊚ |
| Creaky feel after cleansing | ⊚ | ⊚ | ⊚ | ⊚ | ⊚ | ⊚ | ⊚ |
| Storage stability (40° C.) | ○ | ○ | ○ | ○ | ○ | ○ | ○ |
| Storage stability (25° C.) | ○ | ○ | ○ | ○ | ○ | ○ | ○ |
| Storage stability (5° C.) | ○ | ○ | ○ | ○ | ○ | ○ | ○ |

TABLE 5

(% by mass)

| | Examples | | | | | |
|---|---|---|---|---|---|---|
| | 8 | 9 | 10 | 11 | 12 | 13 |
| Polyglycerin oleic acid ester Analysis Example 1, Hydroxyl value: 608 | | | 12.0 | | | |
| Polyglycerin oleic acid ester Analysis Example 2, Hydroxyl value: 586 | | | | | | |
| Polyglycerin oleic acid esters¥ Analysis Example 3, Hydroxyl value: 592 | | | | | | |
| Polyglycerin oleic acid ester Analysis Example 1, Hydroxyl value: 485 | | 22.0 | | | | |
| Polyglycerin isopalmitic acid ester Analysis Example 1, Hydroxyl value: 622 | | | | | | |
| Polyglycerin isostearic acid ester Analysis Example 1, Hydroxyl value: 631 | 13.0 | | | | | |
| Polyglycerin isostearic acid ester Analysis Example 1, Hydroxyl value: 476 | | | | 10.0 | 20.0 | 25.0 |
| Diglycerin isostearic acid ester Hydroxyl value: 410 | | | 8.0 | | | |
| Glycerin oleic acid ester Hydroxyl value: 295 | 2.0 | | | | | |
| Isooctyl palmitate | 75.0 | 58.0 | | 90.0 | 80.0 | 75.0 |
| Glyceryl tri-2-ethylhexanoate | 10.0 | 20.0 | 80.0 | | | |
| To make | 100 | 100 | 100 | 100 | 100 | 100 |
| Dispersibility in water | ⊚ | ○ | ⊚ | ○ | ○ | ○ |
| Slimy feel | ⊚ | ○ | ⊚ | ○ | ○ | ○ |
| Rinsing feel | ⊚ | ○ | ⊚ | ○ | ○ | ○ |
| Stain removal degree | ⊚ | ⊚ | ⊚ | ⊚ | ⊚ | ⊚ |
| Greasy feel after cleansing | ⊚ | ⊚ | ⊚ | ⊚ | ⊚ | ⊚ |
| Creaky feel after cleansing | ⊚ | ⊚ | ⊚ | ⊚ | ⊚ | ⊚ |
| Storage stability (40° C.) | ○ | ○ | ○ | ○ | ○ | ○ |
| Storage stability (25° C.) | ○ | ○ | ○ | ○ | ○ | ○ |
| storage stability (5° C.) | ○ | ○ | ○ | ○ | ○ | ○ |

TABLE 6

(% by mass)

| | Comparative Examples | | | | | |
|---|---|---|---|---|---|---|
| | 1 | 2 | 3 | 4 | 5 | 6 |
| Polyglycerin oleic acid ester Analysis Comparative Example 1, Hydroxyl value: 610 | 16.0 | | | | | |
| Polyglycerin oleic acid ester Analysis Comparative Example 2, Hydroxyl value: 598 | | 16.0 | | | | |
| Polyglycerin oleic acid ester Analysis Comparative Example 3, Hydroxyl value: 633 | | | 16.0 | | | |
| Polyglycerin oleic acid ester Analysis Comparative Example 1, Hydroxyl value: 482 | | | | 20.0 | | 10.0 |
| Polyglycerin isopalmitic acid ester Analysis Comparative Example 4, Hydroxyl value: 628 | | | | | 15.0 | |
| Polyglycerin isostearic acid ester Analysis Example 1, Hydroxyl value: 423 | | | | | | |
| Polyglycerin myristic acid ester Analysis Example 2, Hydroxyl value: 619 | | | | | | |
| Polyglycerin oleic acid ester Analysis Example 1, Hydroxyl value: 485 | | | | | | |
| Polyglycerin isopalmitic acid ester Analysis Example 1, Hydroxyl value: 720 | | | | | | |
| Diglycerin isostearic acid ester Hydroxyl value: 410 | 4.0 | 4.0 | 4.0 | | 5.0 | |
| Glycerin oleic acid ester Hydroxyl value: 295 | | | | | | |
| Isooctyl palmitate | 80.0 | 80.0 | 80.0 | 60.0 | 60.0 | 60.0 |
| Glyceryl tri-2-ethylhexanoate | | | | 20.0 | 20.0 | 30.0 |
| To make | 100 | 100 | 100 | 100 | 100 | 100 |
| Dispersibility in water | X | □ | X | X | X | X |
| Slimy feel | X | □ | X | X | X | X |
| Rinsing feel | X | □ | X | X | X | X |

TABLE 6-continued (% by mass)

| | Comparative Examples | | | | | |
|---|---|---|---|---|---|---|
| | 1 | 2 | 3 | 4 | 5 | 6 |
| Stain removal degree | □ | Δ | □ | □ | □ | X |
| Greasy feel after cleansing | X | Δ | X | X | X | X |
| Creaky feel after cleansing | Δ | ◯ | Δ | Δ | Δ | □ |
| Storage stability (40° C.) | X | ◯ | X | X | X | X |
| Storage stability (25° C.) | X | ◯ | X | X | X | X |
| Storage stability (5° C.) | X | ◯ | X | X | X | X |

TABLE 7

(% by mass)

| | Comparative Examples | | | | | |
|---|---|---|---|---|---|---|
| | 7 | 8 | 9 | 10 | 11 | 12 |
| Polyglycerin oleic acid ester Analysis Comparative Example 1, Hydroxyl value: 610 | | | | | | |
| Polyglycerin oleic acid ester Analysis Comparative Example 2, Hydroxyl value: 598 | 30.0 | | | | | |
| Polyglycerin oleic acid ester Analysis Comparative Example 3, Hydroxyl value: 633 | | | | | | |
| Polyglycerin oleic acid ester Analysis Comparative Example 1, Hydroxyl value: 482 | | | | | | |
| polyglycerin isopalmitic acid ester Analysis Comparative Example 4, Hydroxyl value: 628 | | | | | | |
| Polyglycerin isostearic acid ester Analysis Example 1, Hydroxyl value: 423 | | 20.0 | | | | |
| Polyglycerin myristic acid ester Analysis Example 2, Hydroxyl value: 619 | | | 16.0 | | | |
| Polyglycerin oleic acid ester Analysis Example 1, Hydroxyl value: 485 | | | | 6.0 | 40.0 | |
| Polyglycerin isopalmitic acid ester Analysis Example 1, Hydroxyl value: 720 | | | | | | 16.0 |
| Diglycerin isostearic acid ester Hydroxyl value: 410 | | | | | | |
| Glycerin oleic acid ester Hydroxyl value: 295 | 10.0 | | 4.0 | | | 4.0 |
| Isooctyl palmitate | 40.0 | 70.0 | 80.0 | 85.0 | 55.0 | 80.0 |
| Glyceryl tri-2-ethylhexanoate | 20.0 | 10.0 | | 9.0 | 5.0 | |
| To make | 100 | 100 | 100 | 100 | 100 | 100 |
| Dispersibility in water | □ | □ | □ | X | X | ◯ |
| Slimy feel | □ | □ | □ | □ | □ | ◎ |
| Rinsing feel | □ | □ | □ | X | □ | ◎ |
| Stain removal degree | Δ | □ | Δ | X | □ | Δ |
| Greasy feel after cleansing | □ | X | Δ | Δ | Δ | Δ |
| Creaky feel after cleansing | ◯ | ◯ | ◯ | ◯ | ◯ | Δ |
| Storage stability (40° C.) | ◯ | ◯ | X | ◯ | ◯ | X |
| Storage stability (25° C.) | ◯ | ◯ | ◯ | ◯ | ◯ | ◯ |
| storage stability (5° C.) | ◯ | ◯ | ◯ | ◯ | ◯ | ◯ |

(1) Dispersibility in water: Each of the cleansing cosmetic compositions (5 ml) thus obtained was dispersed in water (50 ml) and stirred for 3 seconds. The state was observed and evaluated according to the following evaluation criteria.

<Evaluation Criteria>

◎: quickly self-emulsified and uniformly dispersed

◯: uniformly dispersed within 10 seconds

Δ: self-emulsified but a white gel-like material is suspended

□: self-emulsified with difficulty and a white gel-like material and an oily material are suspended X: not self-emulsified and an oily material is suspended (2) Sensory evaluation: After applying each of the cleansing cosmetic compositions to the position coated with a water-proof mascara of 10 subjects, the coated portion was massaged repeatedly while sliding hands on the coated portion softly from side to side 10 times, and an operation of wetting the coated portion with enough lukewarm water in the palm of hands was repeatedly conducted 3 times. Then, water is absorbed with a towel. During a series of operations, slimy feel, rinsing feel, stain removal degree, greasy feel after cleansing and creaky feel after cleansing were evaluated by 5-rank criteria.

Slimy Feel:

| <Score> | <Average score> |
|---|---|
| 4: no slimy feel | ◎: 3.5 to 4.0 |
| 3: substantially no slimy feel | ◯: 3.0 to 3.4 |
| 2: somewhat slimy feel | Δ: 2.0 to 2.9 |
| 1: slimy feel | □: 1.0 to 1.9 |
| 0: strong slimy feel | X: 0.0 to 0.9 |

Rinsing Feel:

| <Score> | <Average score> |
|---|---|
| 4: very easy to rinse | ◎: 3.5 to 4.0 |
| 3: easy to rinse | ◯: 3.0 to 3.4 |
| 2: slightly hard to rinse | Δ: 2.0 to 2.9 |
| 1: hard to rinse | □: 1.0 to 1.9 |
| 0: very hard to rinse | X: 0.0 to 0.9 |

Stain Removal Degree:

| <Score> | <Average score> |
| --- | --- |
| 4: stains were removed completely | ◉: 3.5 to 4.0 |
| 3: stains were removed substantially completely | ○: 3.0 to 3.4 |
| 2: less stains are remained | Δ: 2.0 to 2.9 |
| 1: stains are remained | □: 1.0 to 1.9 |
| 0: stains are scarcely removed | X: 0.0 to 0.9 |

Greasy Feel After Cleansing:

| <Score> | <Average score> |
| --- | --- |
| 4: no greasy feel | ◉: 3.5 to 4.0 |
| 3: substantially no greasy feel | ○: 3.0 to 3.4 |
| 2: somewhat greasy feel | Δ: 2.0 to 2.9 |
| 1: greasy feel | □: 1.0 to 1.9 |
| 0: strong greasy feel | X: 0.0 to 0.9 |

Creaky Feel After Cleansing:

| <Score> | <Average score> |
| --- | --- |
| 4: no creaky feel | ◉: 3.5 to 4.0 |
| 3: substantially no creaky feel | ○: 3.0 to 3.4 |
| 2: somewhat creaky feel | Δ: 2.0 to 2.9 |
| 1: creaky feel | □: 1.0 to 1.9 |
| 0: strong creaky feel | X: 0.0 to 0.9 |

(3) Storage stability: After storing at 5° C., 25° C. or 40° C. for 6 months, it was observed whether or not separation or precipitation of an oil layer occurs.
Stable: ○
Precipitation or two-layer separation occurs: X Using the same polyglycerin fatty acid esters as in Example 1, cleansing compositions which are not within the scope of the present invention were prepared. The evaluation results are shown in Table 8 (Comparative Examples 13, 14 and 15).

TABLE 8

| % by mass | | | |
| --- | --- | --- | --- |
| | Comparative Examples | | |
| | 13 | 14 | 15 |
| Polyglycerin oleic acid ester Analysis Example 1, Hydroxyl value: 608 | 16 | 16 | 16 |
| Diglycerin isostearic acid ester Hydroxyl value: 410 | 4 | 4 | 4 |
| Glycerin | 5 | 20 | 20 |
| 1,3-butylene glycol | 10 | 7 | 10 |
| Water | 30 | 3 | |
| Isooctyl palmitate | 30 | 50 | 50 |
| Cetanol | 5 | | |
| To make | 100 | 100 | 100 |
| Dispersibility in water | □ | Δ | □ |
| Slimy feel | □ | Δ | □ |
| Rinsing feel | □ | Δ | □ |
| Stain removal degree | □ | □ | □ |
| Greasy feel after cleansing | □ | □ | □ |
| Creaky feel after cleansing | ○ | ○ | □ |
| Storage stability (40° C.) | X | X | X |
| Storage stability (25° C.) | ○ | ○ | X |
| Storage stability (5° C.) | ○ | ○ | X |
| Electric conductivity | 2.0 | 0.5 | — |
| Solubility in hexane | X | X | — |

(4) Electric conductivity: Electric conductivity was measured by using LACOM conductivity meter ECScanPure+ manufactured by AS ONE CORPORATION.

(5) Solubility in hexane: Solubility in hexane was evaluated by the following procedure. That is, one or two drops of the product of the present invention were added to a 10 ml of a hexane solution using Komagome type pipette and, after slightly stirring, it was observed whether or not the product of the present invention was uniformly dissolved.

In order to confirm that the cleansing cosmetic compositions of Examples 1 to 13 and Comparative Examples 1 to 12 were oily cosmetic compositions, electric conductivity and solubility in hexane were examined. As a result, it was found that all the cleansing cosmetic compositions had electric conductivities of 0.1 μS/cm or less and also dissolved and dispersed in hexane. Therefore, it was recognized that the cleansing cosmetic compositions of Examples 1 to 13 and Comparative Examples 1 to 12 were oily.

The cleansing cosmetic composition of Comparative Example 13 was an oil-in-water type cream and the cleansing cosmetic composition of Comparative Example 14 was a gel including an aqueous polyhydric alcohol continuous phase. As is apparent from the results of electric conductivity and solubility in hexane in Table 8, it was recognized that both of them were not oily. Since the cleansing cosmetic composition of Comparative Example 15 was immediately separated, it was impossible to measure.

As shown in Examples 1 to 13, the oily liquid cleansing cosmetic compositions containing the oily component and the specific polyglycerin fatty acid ester exhibited satisfactory stain removal degree and were free from greasy feel and creaky feel after cleansing, and were also free from slimy feel upon washing out and were easily rinsed, and were therefore excellent in tactile sensation. Moreover, the oily liquid cleansing cosmetic compositions were excellent in storage stability at 5° C., 25° C. and 40° C. On the contrary, the cleansing cosmetic compositions containing the polyglycerin fatty acid esters shown in Comparative Examples 1 to 12 were not excellent oily liquid cleansing cosmetic compositions because the objects of the present invention could not be attained.

It was confirmed that the oily liquid cleansing cosmetic composition of the present invention was excellent in affinity with the cosmetic composition and was therefore an excellent cosmetic composition.

Example of Cleansing Cosmetic Composition

The respective components were added according to the following formulation, dissolved by heating at a temperature of 70 to 80° C. under sufficient stirring and then cooled to room temperature with stirring to prepare a cleansing cosmetic composition.

Example 14

| Formulation of oily liquid cleansing cosmetic composition | |
|---|---|
| | (Unit: g) |
| Polyglycerin oleic acid ester used in Example 1 | 15.0 |
| Diglycerin oleic acid ester (Hydroxyl value: 410) | 2.0 |
| Soybean lecithin (PC content: 60%) | 1.0 |
| Palmityl isooctylate | 39.5 |
| Diisooctylic acid neopentyl glycol | 20.0 |
| Liquid paraffin | 5.0 |
| Isononyl isononanoate | 15.0 |
| Cyclotetrapolysiloxane | 0.5 |
| Natural vitamin E | 1.0 |
| Perfume | 0.5 |
| Purified water | 0.5 |
| To make | 100.0 |

20 expert panelists used the oily liquid cleansing cosmetic composition of Example 14 of the present invention. As a result of the evaluation, all tactile sensations were rated ⊙ (no slimy feel, very easy to rinse, stains were completely removed, no greasy feel, no creaky feel) and also storage stability was rated as ○ (stable) at all temperatures.

Comparative Example of Cleansing Cosmetic Composition

Comparative Example 16

Using polyethylene glycol (PEG average polymerization amount: 15) isostearic acid ester in place of the polyglycerin oleic acid ester of Example 11, an oily liquid cleansing cosmetic composition was prepared. With respect to the resulting cleansing cosmetic composition, stain removal degree was rated as ⊙ (stains were completely removed), but creaky feel was rated as X (strong creaky feel) and tactile sensation was rated as Δ (somewhat slimy feel, slightly hard to rinse, somewhat greasy feel).

Examples and Comparative Examples of Bath Cosmetic Compositions

Examples 15 to 24 and Comparative Examples 17 to 28

The bath cosmetic compositions of Examples 15 to 24 and Comparative Examples 17 to 28 were prepared in the same manner as in case of the cleansing cosmetic compositions according to the same formulations as in Examples 1 to 10 and Comparative Examples 1 to 12 (components, amounts). The evaluation results are shown in Table 9 and Table 10.

(1) Dispersibility in bath water: Each of the bath cosmetic compositions (20 ml) thus obtained was dispersed in bath water (200 l) at 40° C. and, after stirring with bare hands for 3 seconds, the state was observed and evaluated according to the following evaluation criteria.

<Evaluation Criteria>
⊙: quickly self-emulsified and uniformly dispersed
○: uniformly dispersed within 10 seconds
Δ: self-emulsified but a white gel-like material is suspended
□: self-emulsified with difficulty and a white gel-like material and an oily material are suspended
X: not self-emulsified and an oily material is suspended (2) Tactile sensation: 10 subjects were asked to take a bath for 5 minutes and moist feel and greasy feel after bathing were evaluated according to the following criteria.

Moist Feel:

| <Score> | <Average score> |
|---|---|
| 4: remarkable moist feel | ⊙: 3.5 to 4.0 |
| 3: moist feel | ○: 3.0 to 3.4 |
| 2: somewhat moist feel | Δ: 2.0 to 2.9 |
| 1: substantially no moist feel | □: 1.0 to 1.9 |
| 0: no moist feel | X: 0.0 to 0.9 |

Greasy Feel:

| <Score> | <Average score> |
|---|---|
| 4: no greasy feel | ⊙: 3.5 to 4.0 |
| 3: substantially no greasy feel | ○: 3.0 to 3.4 |
| 2: somewhat greasy feel | Δ: 2.0 to 2.9 |
| 1: greasy feel | □: 1.0 to 1.9 |
| 0: strong greasy feel | X: 0.0 to 0.9 |

The products of the present invention were excellent in all items, whereas the comparative products were insufficient in all items.

(3) Storage stability: After storing at 5° C., 25° C. and 40° C. for 6 months, it was observed whether or not separation or precipitation of an oil layer occurs.
Stable: ○
Precipitation or two-layer separation occurs: X In order to confirm that the bath cosmetic compositions of Examples 15 to 24 and Comparative Examples 17 to 28 were oily cosmetic compositions, electric conductivity and solubility in hexane were examined. As a result, it was confirmed that all bath cosmetic compositions had electric conductivities of 0.1 μS/cm or less and also dissolved and dispersed in hexane. Therefore, it was recognized that the bath cosmetic compositions of Examples 15 to 24 and Comparative Examples 17 to 28 were oily.

TABLE 9

| | Examples | | | | | | | | | |
|---|---|---|---|---|---|---|---|---|---|---|
| | 15 | 16 | 17 | 18 | 19 | 20 | 21 | 22 | 23 | 24 |
| Dispersibility in bath water | ⊙ | ⊙ | ⊙ | ○ | ○ | ○ | ○ | ⊙ | ○ | ⊙ |
| Moist feel | ⊙ | ⊙ | ⊙ | ⊙ | ⊙ | ⊙ | ○ | ⊙ | ⊙ | ⊙ |
| Greasiness | ⊙ | ⊙ | ⊙ | ⊙ | ⊙ | ⊙ | ○ | ⊙ | ⊙ | ⊙ |
| Storage stability (40° C.) | ○ | ○ | ○ | ○ | ○ | ○ | ○ | ○ | ○ | ○ |
| Storage stability (25° C.) | ○ | ○ | ○ | ○ | ○ | ○ | ○ | ○ | ○ | ○ |
| Storage stability (5° C.) | ○ | ○ | ○ | ○ | ○ | ○ | ○ | ○ | ○ | ○ |

TABLE 10

| | Comparative Examples | | | | | | | | | | | |
|---|---|---|---|---|---|---|---|---|---|---|---|---|
| | 17 | 18 | 19 | 20 | 21 | 22 | 23 | 24 | 25 | 26 | 27 | 28 |
| Dispersibility in bath water | X | □ | X | X | X | X | □ | □ | □ | X | X | □ |
| Moist feel | X | Δ | X | X | X | X | Δ | Δ | Δ | X | □ | □ |
| Greasiness | X | Δ | X | X | X | X | □ | □ | □ | X | □ | □ |
| Storage stability (40° C.) | X | ○ | X | X | X | X | ○ | ○ | X | ○ | ○ | X |
| Storage stability (25° C.) | X | ○ | X | X | X | X | ○ | ○ | ○ | ○ | ○ | ○ |
| Storage stability (5° C.) | X | ○ | X | X | X | X | ○ | ○ | ○ | ○ | ○ | ○ |

Example of Bath Cosmetic Composition

The respective components were added according to the following formulation, dissolved by heating at a temperature of 70 to 80° C. under sufficient stirring and then cooled to room temperature with stirring to prepare a bath cosmetic composition.

Example 25

| Formulation of bath cosmetic composition | |
|---|---|
| | (Unit: g) |
| Polyglycerin oleic acid ester used in Example 1 | 16.0 |
| Diglycerin oleic acid ester (Hydroxyl value: 410) | 2.0 |
| Soybean lecithin (PC content: 60%) | 0.5 |
| Isostearyl palmitate | 39.0 |
| Dicapric acid neopentyl glycol | 20.0 |
| Squalane | 5.0 |
| Glyceryl tri(caprylate · caprate) | 15.0 |
| High-oleic safflower oil | 1.0 |
| Perfume | 1.0 |
| Purified water | 0.5 |
| To make | 100.0 |

20 expert panelists used the bath cosmetic composition of Example 25 of the present invention. As a result of the evaluation, dispersibility in bath water was rated as ⊙ (quickly self-emulsified and uniformly dispersed) and moist feel was rated as ⊙ (excellent moist feel) and also greasy feel was rated as ⊙ (no greasy feel). Storage stability was rated as ○ (stable) at all temperatures.

It was confirmed that the resulting bath cosmetic composition had electric conductivity at 25° C. of 0.1 μS/cm or less and also dissolved and dispersed in hexane. Therefore, it was recognized that the bath cosmetic composition was oily.

As shown in Examples 15 to 25, the bath cosmetic compositions containing the oily component and the specific polyglycerin fatty acid ester were excellent in dispersibility in bath water and storage stability, and were also excellent in tactile sensation such as moist feel. On the contrary, the bath cosmetic compositions containing the polyglycerin fatty acid ester shown in Comparative Examples 17 to 28 were inferior in dispersibility in bath water, stability and tactile sensation and were unsuited for the bath cosmetic composition.

INDUSTRIAL APPLICABILITY

The self emulsification type oily liquid cosmetic composition of the present invention can be widely used in the fields of chemical products and drugs.

The invention claimed is:

1. A self emulsification type oily liquid cosmetic composition comprising 8 to 30% by mass of a component A and 50 to 92% by mass of a component B,
    wherein the component A is a polyglycerin fatty acid ester having a hydroxyl value of 450 to 700, and a branched fatty acid residue having 16 to 18 carbon atoms and/or a liner unsaturated fatty acid residue having 16 to 18 carbon atoms accounting for 50 to 100% by mass of total constituent fatty acid residues, and in a polyglycerin constituting the polyglycerin fatty acid ester, a total content of a polyglycerin cyclic compound of a dimer and a trimer is from 0 to 3% based on the entire polyglycerin, a total content of a polyglycerin of a undecamer or a higher multimer is from 10 to 30% based on the entire polyglycerin, and each content of a polyglycerin of a tetramer to a decamer is from 4 to 20% based on the entire polyglycerin, and
    the component B is an oily component.

2. The self emulsification type oily liquid cosmetic composition according to claim 1, wherein the branched fatty acid residue having 16 to 18 carbon atoms is an isostearic acid residue and the linear unsaturated fat acid residue having 16 to 18 carbon atoms is an oleic acid residue.

3. The self emulsification type oily liquid cosmetic composition according to claim 1, wherein a content of water is from 0 to 2% by mass.

4. The self emulsification type oily liquid cosmetic composition according to claim 1, which contains no water.

5. The self emulsification type oily liquid cosmetic composition according to claim 1, which has electric conductivity at 25° C. of 0.1 μS/cm or less and has properties capable of uniformly dissolving and dispersing in a hydrocarbon solvent.

6. The self emulsification type oily liquid cosmetic composition according to claim 1, wherein a content of a hydrocarbon oil in the oily component as the component B is less than 10% by mass based on the self emulsification type oily liquid cosmetic composition.

7. The self emulsification type oily liquid cosmetic composition according to claim 1, which is a cleansing cosmetic composition.

8. The self emulsification type oily liquid cosmetic composition according to claim 1, which is a bath cosmetic composition.

9. A self emulsification type oily liquid cosmetic composition comprising 10 to 25% by mass of a component A and 65 to 85% by mass of a component B,
    wherein the component A is a polyglycerin fatty acid ester having a hydroxyl value of 450 to 700, and a branched fatty acid residue having 16 to 18 carbon atoms and/or a linear unsaturated fatty acid residue having 16 to 18 carbon atoms accounting for 50 to 100% by mass of total constituent fatty acid residues, and in a polyglycerin constituting the polyglycerin fatty acid ester, a total content of a polyglycerin cyclic compound of a dimer and a trimer is from 0 to 3% based on the entire polyglycerin, a total content of a polyglycerin of a undecamer or a higher multimer is from 10 to 30% based on the entire polyglycerin, and each content of a polyglycerin of a tetramer to a decamer is from 4 to 20% based on the entire polyglycerin, and the component B is an oily component.

10. The self emulsification type oily liquid cosmetic composition according to claim 9, further comprising lecithin in a content of 1 to 10% by mass based on a content of the component A.

11. The self emulsification type oily liquid cosmetic composition according to claim 9, wherein a content of water is from 0 to 2% by mass.

12. The self emulsification type oily liquid cosmetic composition according to claim 9, which contains no water.

13. The self emulsification type oily liquid cosmetic composition according to claim 9, which has electric conductivity at 25° C. of 0.1 μS/cm or less and has properties capable of uniformly dissolving and dispersing in a hydrocarbon solvent.

14. The self emulsification type oily liquid cosmetic composition according to claim 9, wherein a content of a hydrocarbon oil in the oily component as the component B is less than 10% by mass based on the self emulsification type oily liquid cosmetic composition.

15. The self emulsification type oily liquid cosmetic composition according to claim 9, which is a cleansing cosmetic composition.

16. The self emulsification type oily liquid cosmetic composition according to claim 9, which is a bath cosmetic composition.

17. A self emulsification type oily liquid cosmetic composition comprising 8 to 30% by mass of a component A, 65 to 90% by mass of a component B and 0.1 to 100% by mass of a component C based on a content of the component A, wherein the component A is a polyglycerin fatty acid ester having a hydroxyl value of 550 to 700, and a branched fat acid residue having 16 to 18 carbon atoms and/or a linear unsaturated fatty acid residue having 16 to 18 carbon atoms accounting for 50 to 100% by mass of total constituent fat acid residues, and in a polyglycerin constituting the polyglycerin fat acid ester, a total content of a polyglycerin cyclic compound of a dimer and a trimer is from 0 to 3% based on the entire polyglycerin, a total content of a polyglycerin of a undecamer or a higher multimer is from 10 to 30% based on the entire polyglycerin, and each content of a polyglycerin of a tetramer to a decamer is from 4 to 20% based on the entire polyglycerin, the component B is an oily component, and the component C is a polyhydric alcohol fatty acid ester having a hydroxyl value of 100 to 500 (excluding the component A) and/or a polyhydric alcohol alkyl ether having a hydroxyl value of 100 to 500.

18. The self emulsification type oily liquid cosmetic composition according to claim 17, wherein a content of water is from 0 to 2% by mass.

19. The self emulsification type oily liquid cosmetic composition according to claim 17, which contains no water.

20. The self emulsification type oily liquid cosmetic composition according to claim 17, which has electric conductivity at 25° C. of 0.1 μS/cm or less and has properties capable of uniformly dissolving and dispersing in a hydrocarbon solvent.

21. The self emulsification type oily liquid cosmetic composition according to claim 17, wherein a content of a hydrocarbon oil in the oily component as the component B is less than 10% by mass based on the self emulsification type oily liquid cosmetic composition.

22. The self emulsification type oily liquid cosmetic composition according to claim 17, which is a cleansing cosmetic composition.

23. The self emulsification type oily liquid cosmetic composition according to claim 17, which is a bath cosmetic composition.

24. A self emulsification type oily liquid cosmetic composition comprising 10 to 25% by mass of a component A, 65 to 85% by mass of a component B and 0.1 to 100% by mass of a component C based on a content of the component A, wherein the component A is a polyglycerin fatty acid ester having a hydroxyl value of 550 to 700, and a branched fatty acid residue having 16 to 18 carbon atoms and/or a linear unsaturated fatty acid residue having 16 to 18 carbon atoms accounting for 50 to 100% by mass of total constituent fatty acid residues, and in a polyglycerin constituting the polyglycerin fatty acid ester, a total content of a polyglycerin cyclic compound of a dimer and a trimer is from 0 to 3% based on the entire polyglycerin, a total content of a polyglycerin of a undecamer or a higher multimer is from 10 to 30% based on the entire polyglycerin, and each content of a polyglycerin of a tetramer to a decamer is from 4 to 20% based on the entire polyglycerin, the component B is an oily component, and the component C is a polyhydric alcohol fatty acid ester having a hydroxyl value of 100 to 500 (excluding the component A) and/or a polyhydric alcohol alkyl ether having a hydroxyl value of 100 to 500.

25. The self emulsification type oily liquid cosmetic composition according to claim 24, further comprising lecithin in a content of 1 to 10% by mass based on a content of the component A.

26. The self emulsification type oily liquid cosmetic composition according to claim 24, wherein a content of water is from 0 to 2% by mass.

27. The self emulsification type oily liquid cosmetic composition according to claim 24, which contains no water.

28. The self emulsification type oily liquid cosmetic composition according to claim 24, which has electric conductivity at 25° C. of 0.1 μS/cm or less and has properties capable of uniformly dissolving and dispersing in a hydrocarbon solvent.

29. The self emulsification type oily liquid cosmetic composition according to claim 24, wherein a content of a hydrocarbon oil in the oily component as the component B is less than 10% by mass based on the self emulsification type oily liquid cosmetic composition.

30. The self emulsification type oily liquid cosmetic composition according to claim 24, which is a cleansing cosmetic composition.

31. The self emulsification type oily liquid cosmetic composition according to claim 24, which is a bath cosmetic composition.

* * * * *